(12) United States Patent
Ogawa et al.

(10) Patent No.: US 10,316,778 B2
(45) Date of Patent: Jun. 11, 2019

(54) ESTIMATION DEVICE, ESTIMATION METHOD, COMPUTER-READABLE NON-TRANSITORY MEDIUM, ENGINE AND MOVEMENT DEVICE

(71) Applicant: FUJITSU LIMITED, Kawasaki-shi, Kanagawa (JP)

(72) Inventors: Masatoshi Ogawa, Zama (JP); Noriyasu Aso, Isehara (JP); Hiromitsu Soneda, Atsugi (JP); Takeo Kasajima, Machida (JP); Masao Kondo, Sagamihara (JP)

(73) Assignee: FUJITSU LIMITED, Kawasaki (JP)

( * ) Notice: Subject to any disclaimer, the term of this patent is extended or adjusted under 35 U.S.C. 154(b) by 175 days.

(21) Appl. No.: 15/232,842

(22) Filed: Aug. 10, 2016

(65) Prior Publication Data

US 2017/0089283 A1    Mar. 30, 2017

(30) Foreign Application Priority Data

Sep. 24, 2015 (JP) .................................. 2015-187455

(51) Int. Cl.
  *F02D 41/14* (2006.01)
  *G01N 25/22* (2006.01)
  (Continued)

(52) U.S. Cl.
  CPC ....... *F02D 41/1447* (2013.01); *F02D 35/023* (2013.01); *F02D 41/402* (2013.01);
  (Continued)

(58) Field of Classification Search
  CPC .......... F02D 41/402–405; F02D 41/28; F02D 41/1447; F02D 2041/1423;
  (Continued)

(56) References Cited

U.S. PATENT DOCUMENTS

2005/0022789 A1* 2/2005 Palma ................... F02D 35/024
                                                      123/435
2005/0273244 A1* 12/2005 Cesario ............... F02D 41/1405
                                                      701/106
(Continued)

FOREIGN PATENT DOCUMENTS

JP    2007-239524    9/2007
JP    2007-248119    9/2007
(Continued)

*Primary Examiner* — Mahmoud Gimie
*Assistant Examiner* — Joshua Campbell
(74) *Attorney, Agent, or Firm* — Fujitsu Patent Center

(57) ABSTRACT

An estimation device includes: a memory and a processor, wherein the processor is configured to execute a process including: determining a point of a burning having a higher peak in a predetermined range of a heat release rate based on a peak of a burning having a smaller peak, in a heat release rate waveform in an internal combustion engine that performs a multiple-stage fuel injection; calculating a tangential line of the heat release rate waveform at the point; setting a predetermined point on the tangential line as an initial value for identifying a model parameter of a heat release rate model; identifying the model parameter so that a difference between a calculation value of the heat release rate model and the heat release rate waveform is reduced with use of the initial value; and estimating a heat release rate with a result of an identification of the identifying.

14 Claims, 18 Drawing Sheets

(51) Int. Cl.
*F02D 41/40* (2006.01)
*F02D 35/02* (2006.01)
*F02D 41/24* (2006.01)
*F02D 41/28* (2006.01)

(52) U.S. Cl.
CPC ........... *G01N 25/22* (2013.01); *F02D 41/247* (2013.01); *F02D 41/28* (2013.01); *F02D 41/40* (2013.01); *F02D 41/403* (2013.01); *F02D 41/405* (2013.01); *F02D 2041/1423* (2013.01); *F02D 2041/1433* (2013.01); *F02D 2041/286* (2013.01); *Y02T 10/44* (2013.01)

(58) Field of Classification Search
CPC ....... F02D 2041/1433; F02D 2041/286; F02D 35/023; G01N 25/22; Y02T 10/44
USPC .......................................................... 701/102
See application file for complete search history.

(56) References Cited

U.S. PATENT DOCUMENTS

| | | | |
|---|---|---|---|
| 2008/0216557 A1* | 9/2008 | Wang | F02D 35/025 73/23.31 |
| 2010/0242912 A1* | 9/2010 | Folkerts | F02D 35/023 123/435 |
| 2012/0150414 A1* | 6/2012 | Huang | F02D 35/024 701/101 |
| 2014/0060488 A1* | 3/2014 | Katzenberger | F02D 41/2096 123/456 |
| 2015/0122000 A1* | 5/2015 | Willimowski | F02M 51/00 73/114.45 |

FOREIGN PATENT DOCUMENTS

| | | | | |
|---|---|---|---|---|
| JP | 2011-106334 | | 6/2011 | |
| JP | WO 2015040804 A1 * | | 3/2015 | ........... F02D 41/247 |

\* cited by examiner

FIG. 15

|  | START TIMING OF MAIN BURNING deg.ATDC | START TIMING OF AFTER-BURNING deg.ATDC |
|---|---|---|
| TRUE VALUE | 2.7 | 36.4 |
| COMPARATIVE EXAMPLE | 0.8 | 12.2 |
| EMBODIMENT | 2.6 | 36.8 |
| REDUCTION RATE OF ERROR | 94.7% | 98.3% |

ESTIMATION DEVICE, ESTIMATION METHOD, COMPUTER-READABLE NON-TRANSITORY MEDIUM, ENGINE AND MOVEMENT DEVICE

CROSS-REFERENCE TO RELATED APPLICATION

This application is based upon and claims the benefit of priority of the prior Japanese Patent Application No. 2015-187455, filed on Sep. 24, 2015, the entire contents of which are incorporated herein by reference.

FIELD

A certain aspect of embodiments described herein relates to an estimation device, an estimation method, a computer-readable non-transitory medium, an engine and a movement device.

BACKGROUND

There is a method using Wiebe function as a method of expressing a heat release rate of an engine (internal combustion engine) with a mathematical formula (for example, see Japanese Patent Application Publication Nos. 2011-106334, 2007-248119 and 2007-239524.

SUMMARY

According to an aspect of the present invention, there is provided an estimation device including a memory and a processor, wherein the processor is configured to execute a process, the process including: determining a point of a burning having a higher peak in a predetermined range of a heat release rate based on a peak of a burning having a smaller peak, in a heat release rate waveform in an internal combustion engine that performs a multiple-stage fuel injection; calculating a tangential line of the heat release rate waveform at the point determined in the determining; setting a predetermined point on the tangential line as an initial value for identifying a model parameter of a heat release rate model; identifying the model parameter so that a difference between a calculation value of the heat release rate model and the heat release rate waveform is reduced with use of the initial value; and estimating a heat release rate corresponding to a predetermined operation condition of the internal combustion engine with a result of an identification of the identifying.

BRIEF DESCRIPTION OF DRAWINGS

FIG. 15 illustrates a calculation result of a start timing of a main burning and a start timing of an after-burning of a comparative example and an embodiment;

DESCRIPTION OF EMBODIMENTS

Torque requested for an engine is determined by an accelerator operation of a driver and so on. A torque-based control is performed by estimating an indicated torque satisfying requested torque. For example, there is a method of expressing the indicated torque with a mathematical model as a method of achieving further improvement of engine performance and reduction of development processes of a control system compared to a conventional method based on a map function. It is possible to calculate the indicated torque from a cylinder pressure per a crank angle. It is possible to calculate the cylinder pressure from a heat release rate that is a changing rate of a heat release amount per a crank angle. It is therefore possible to effectively use the model for high performance of an engine control system and effectiveness of development in the torque-based control if a model estimating the heat release rate with high accuracy can be achieved.

Figure 1:
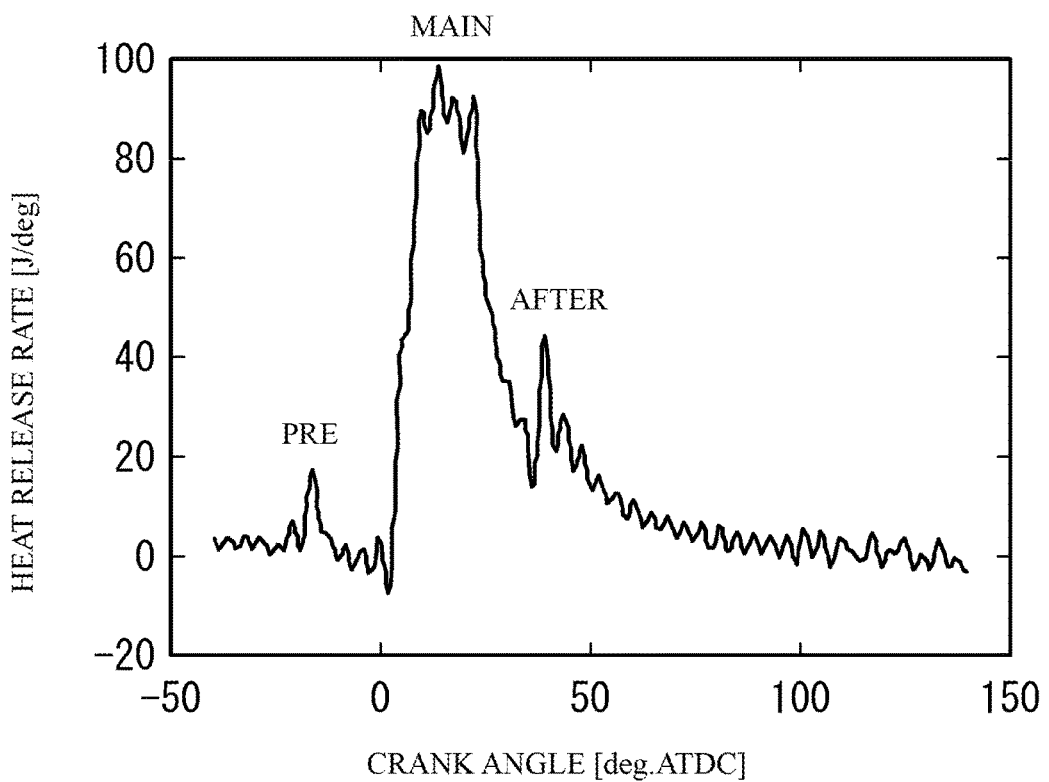
FIG. 1 illustrates a heat release rate waveform.

There is a method using Wiebe function as a method of expressing the heat release rate of an engine with a mathematical model. In an engine, multiple-stage fuel injection is performed for the purpose of high performance. The multiple-stage fuel injection is a fuel injection in which fuel is injected at different crank angles. A waveform of the heat release rate is a complicated waveform as illustrated in FIG. 1. In FIG. 1, a heat release rate waveform of a case of three-stage fuel injection. In an example of FIG. 1, a mountain corresponding to a first fuel injection is a pre-burning. A mountain corresponding to a second fuel injection is a main-burning. A mountain corresponding to a third fuel injection is a combination of an after-burning and a diffusion burning occurring together with the after-burning.

When each burning is expressed by an individual Wiebe function and a calculation result of each Wiebe function is overlapped, it is possible to express an original heat release rate waveform. If generalized, an i-th burning of the heat release rate is expressed as the following formula (1) with use of an fuel injection amount $m_{inj}$, a burning rate $x_{fi}$, a lower heat amount LHV, a shape coefficient m, a burning period $\Delta\theta_i$, a shape coefficient $a_i$, a start timing of fuel injection $\theta_{SOCi}$, and the number of injection N.

$$RoHR_i = m_{inj} \cdot x_{fi} \cdot LHV \cdot \frac{m_i + 1}{\Delta\theta_i} \cdot a_i \cdot \left(\frac{\theta - \theta_{SOC_i}}{\Delta\theta_i}\right)^m \quad \text{[Formula 1]}$$
$$\exp\left\{-a_i \cdot \left(\frac{\theta - \theta_{SOC_i}}{\Delta\theta_i}\right)^{m+1}\right\}$$

A total heat release rate calculated by overlapping the calculation results is expressed as the following formula (2).

$$RoHR_{total} = \sum_{i=1}^{N+1} RoHR_i \quad \text{[Formula 2]}$$

Unknown parameters requiring a parameter identification are a fuel rate $x_f$, a shape coefficient m, a burning period $\Delta\theta$, a shape coefficient a and a start timing of fuel injection $\theta_{SOC}$. Therefore, a problem identifying 5×(N+1) parameters with use of the five parameters with respect to N+1 in which the diffusion burning is added to the number of injections N is solved.

Figure 2:
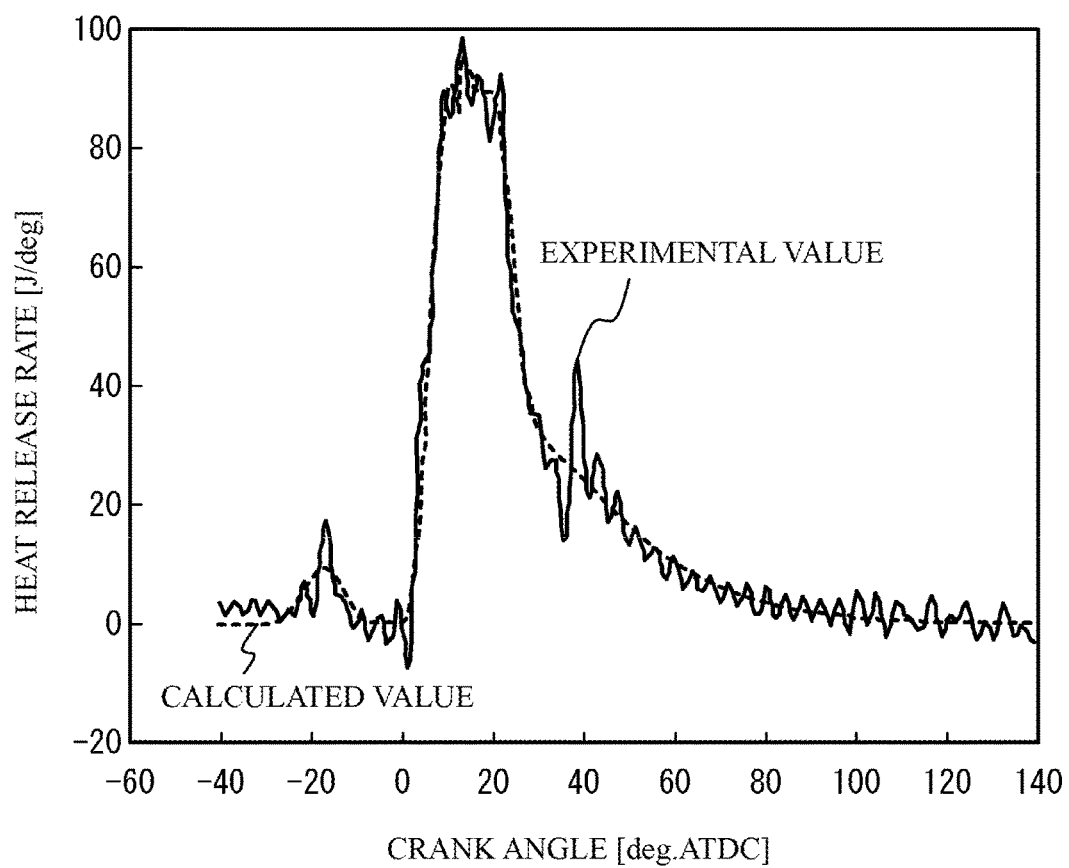
FIG. 2 illustrates an identification result of a model parameter with use of an optimal solver.
Figure 3:
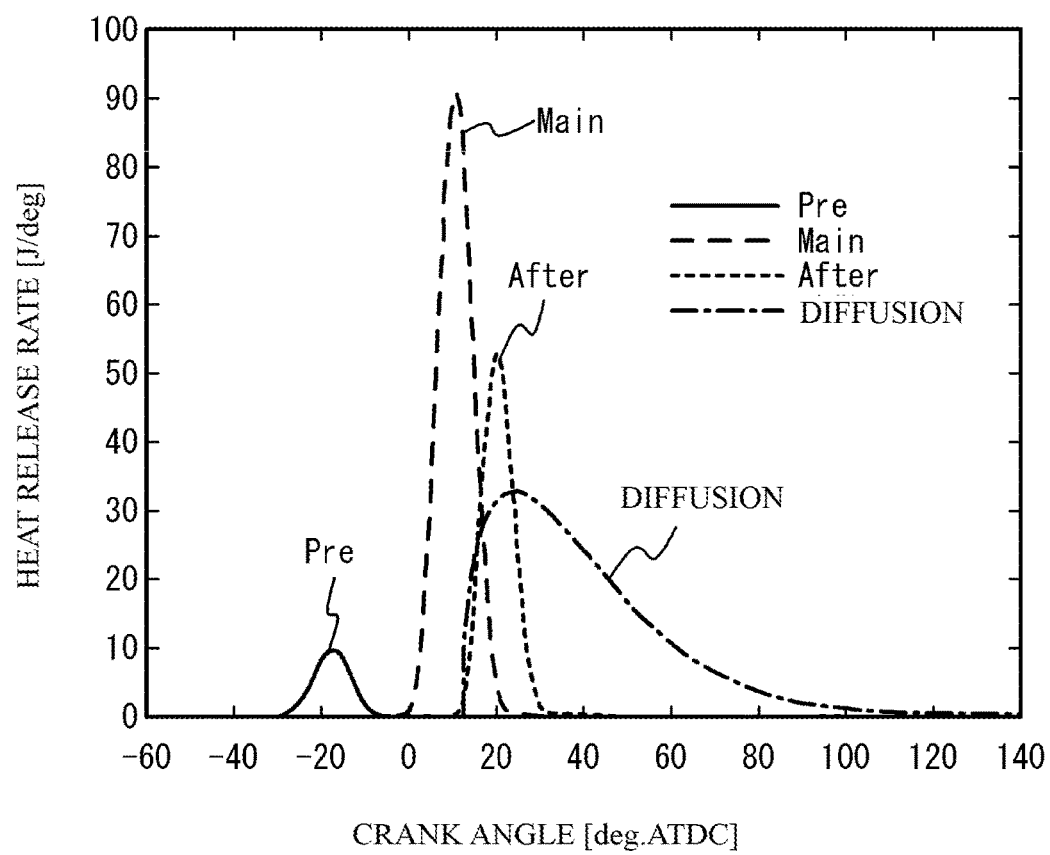
FIG. 3 illustrates an identification result of a model parameter with use of an optimal solver.

FIG. 2 and FIG. 3 illustrate an identification result of the model parameter with use of an optimal solver so that an error between the experimental value and the calculation value of the model is a minimum value in a model parameter identification of the heat release rate of three-stage injection. In FIG. 2 and FIG. 3, it is understood that the start timing of the after-burning is not precise. This is because the number of the model parameters is large, the freedom degree is high, and the heat release waveform includes an oscillation component. There is a problem that a heat release rate model along physical phenomenon cannot be structured in some operation conditions.

A description will be given of an estimation device, an estimation method and an estimation program that are capable of estimating a heat release rate of an internal combustion engine with high accuracy.

Figure 4:
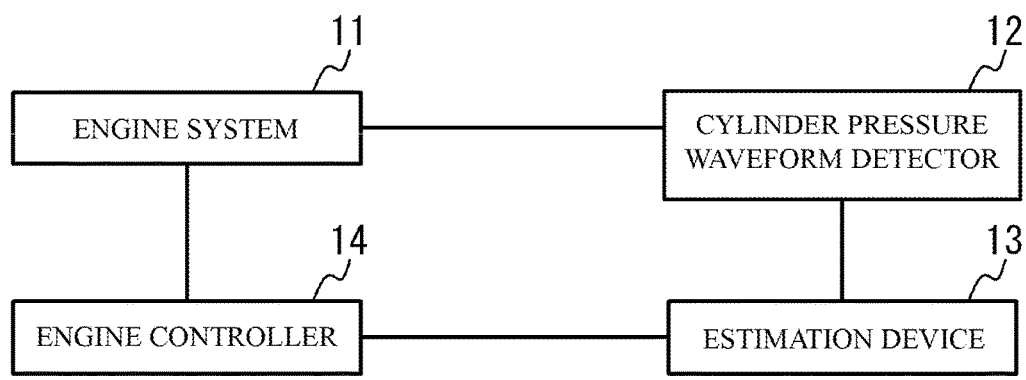
FIG. 4 illustrates a block diagram of an example of an engine to which an estimation device in accordance with an embodiment is applied.

[Embodiment] FIG. 4 illustrates a block diagram of an example of an engine to which an estimation device in accordance with an embodiment is applied. As an example, the embodiment is a diesel engine of three-stage injection. That is, a heat release rate waveform includes a pre-burning, a main burning and an after-burning. An engine 100 has an engine system 11, a cylinder pressure waveform detector 12, an estimation device 13 and an engine controller 14.

The engine system 11 is an engine having one or more cylinders. The engine controller 14 controls the engine system 11. The cylinder pressure waveform detector 12 detects a cylinder pressure waveform of each cylinder from the engine system 11. The estimation device 13 obtains a cylinder pressure waveform from the cylinder pressure waveform detector 12, obtains an operation condition from the engine controller 14, estimates a current heat release rate and gives an estimation result of the heat release rate to the engine controller 14. The engine controller 14 controls the engine system 11 based on the estimation result of the heat release rate and the operation condition.

Figure 5:
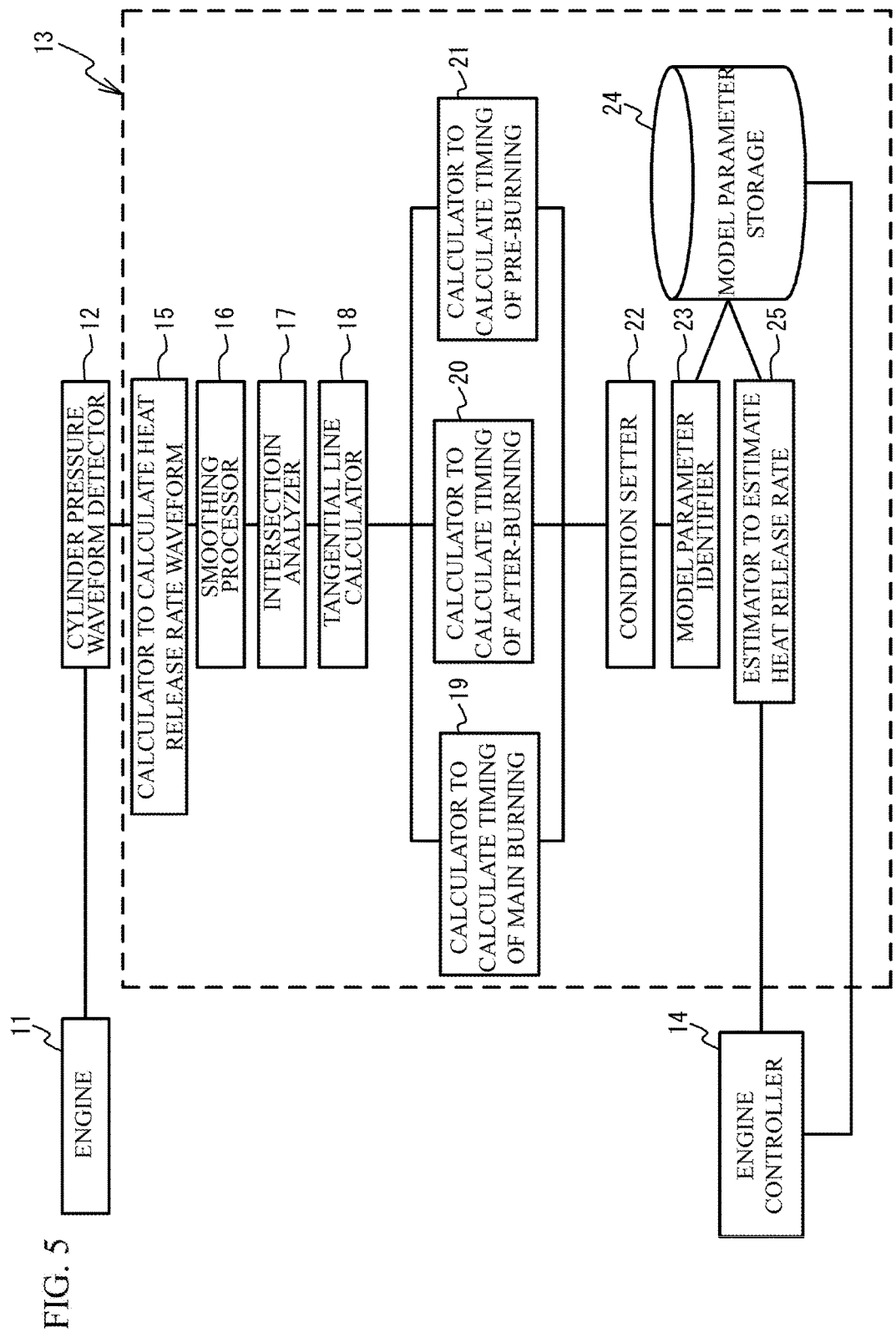
FIG. 5 illustrates a block diagram of an estimation device.

FIG. 5 illustrates a block diagram of the estimation device 13. The estimation device 13 has a calculator 15 to calculate heat release rate waveform, a smoothing processor 16, an intersection analyzer 17, a tangential line calculator 18, a calculator 19 to calculate main burning timing, a calculator 20 to calculate after-burning timing, a calculator 21 to calculate pre-burning timing, a condition setter 22, a model parameter identifier 23, a model parameter storage 24, and a heat release rate estimator 25. A description will be given of details of each operation.

Figure 6:
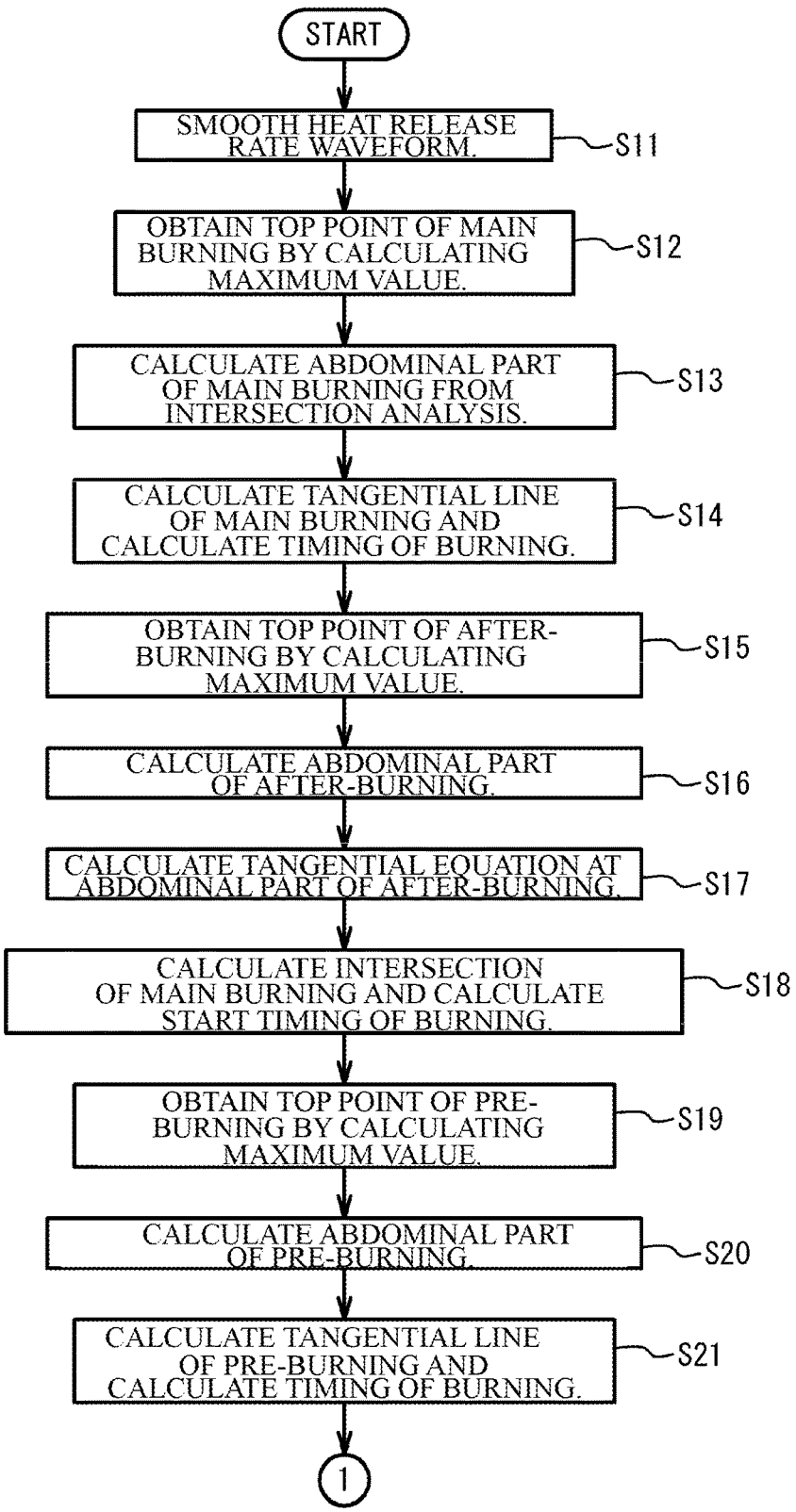
FIG. 6 illustrates a flowchart executed by an estimation device.
Figure 7:
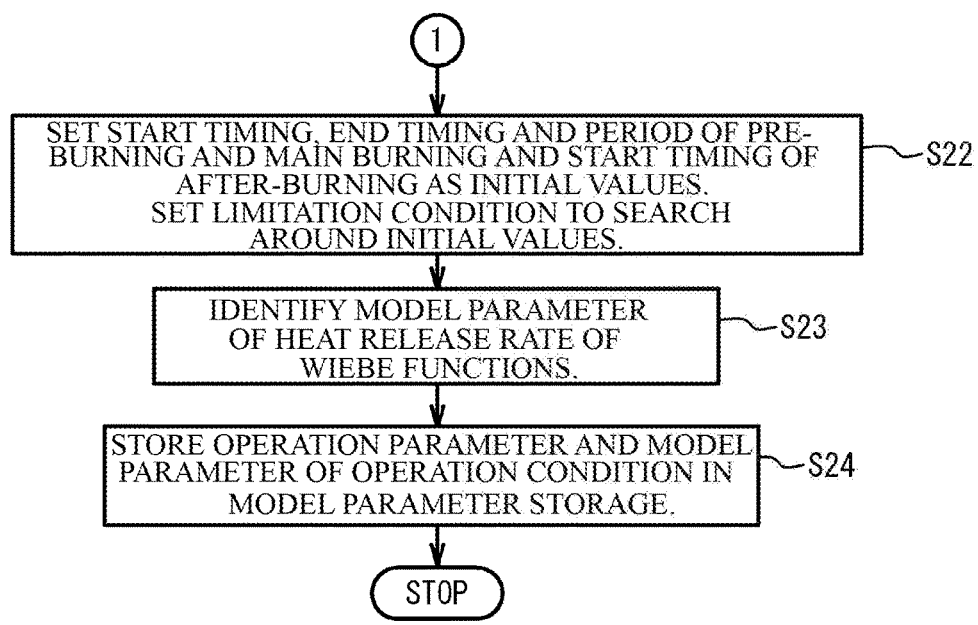
FIG. 7 illustrates a flowchart executed by an estimation device.
Figure 8:
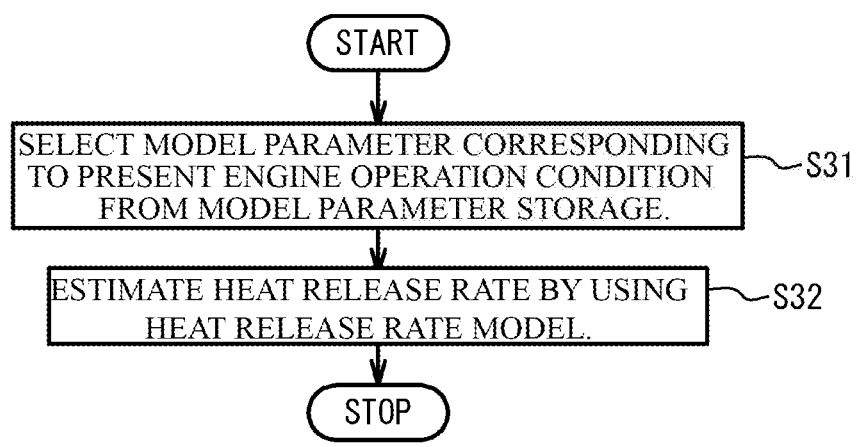
FIG. 8 illustrates a flowchart executed by an estimation device.

FIG. 6 to FIG. 8 illustrate a flowchart executed by the estimation device 13. The estimation device 13 executes a sequence of processes illustrated in FIG. 6 and FIG. 7 at a time interval allowing a data sampling (for example, every 30 seconds). As illustrated in FIG. 6, the calculator 15 to calculate heat release rate waveform calculates an average cylinder pressure from a cylinder pressure at every crank angle of each cylinder detected by the cylinder pressure waveform detector 12, and calculates a heat release rate waveform per a crank angle from the calculation result. Time may be used instead of the crank angle. The smoothing processor 16 smooths the heat release rate waveform at every crank angle calculated by the calculator 15 to calculate heat release rate waveform, and deletes oscillation components such as noise of the heat release rate waveform (Step S11)

Figure 9:
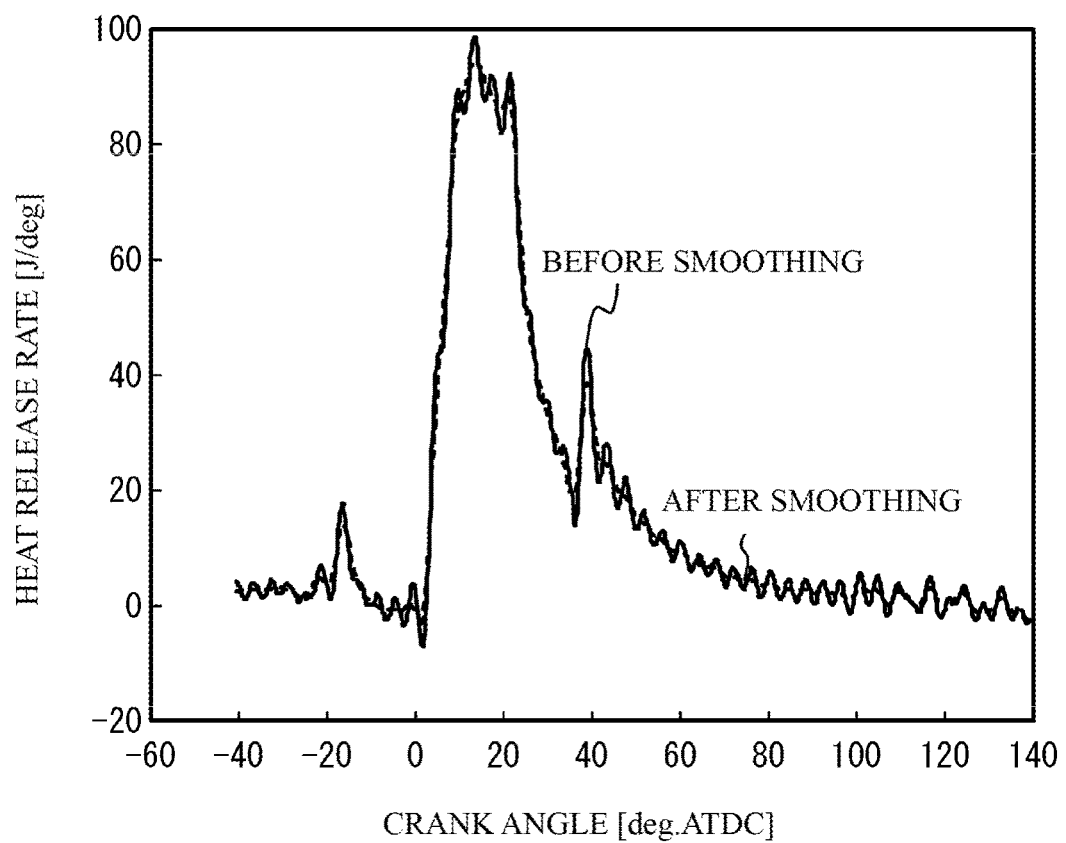
FIG. 9 illustrates an example of a smoothed heat release rate waveform.

As an example of the smoothing process, the embodiment uses a moving average process in which a heat release rate value of each point is replaced by an average of heat release rate values of a predetermined range before and after the point. FIG. 9 illustrates an example of a smoothed heat release rate waveform. As illustrated in FIG. 9, the heat release rate values are smoothed by the smoothing process. With the smoothing process, influence of noise is suppressed. Therefore, an accuracy of the intersection analysis is improved. Another smoothing process such as an arithmetic average may be used.

Next, the intersection analyzer 17 calculates a maximum value of the smoothed heat release rate waveform and sets the maximum value as a top point of the main burning (Step S12). Next, the intersection analyzer 17 prepares a predetermined straight line expressed by the following formula (3). It is preferable that the straight line does not have an inclination. The straight line may have a predetermined inclination expressed by the following formula (4). "$y_{rhr}$" is a heat release rate value. "$x_{crank}$" is a crank angle value. "$\beta_0$" is an intercept.

$$y_{rhr} = \beta_0 \quad (3)$$

$$y_{rhr} = \beta_1 \times x_{crank} \quad (4)$$

Next, the intersection analyzer 17 calculates an intersection point between the heat release rate waveform and the above-mentioned straight line within a range from a closing timing of an inlet valve to an opening timing of an exhaust valve. The intersection analyzer 17 gradually reduces an intercept $\beta_0$ of the straight line corresponding to a position of the heat release rate direction from an intersection between the top of the main burning and the straight line with a predetermined step size. In this case, the intersection analyzer 17 calculates a number of the intersection points between the heat release rate waveform and the straight line at every position of the intercept $\beta_0$. When determination that the number of the intersection points is equal to or more than a first threshold sequentially continues a second threshold times or more, the intersection analyzer 17 sets a point just before a point at which the number of intersection points exceeds the first threshold to an abdominal part of the main burning.

Figure 10:
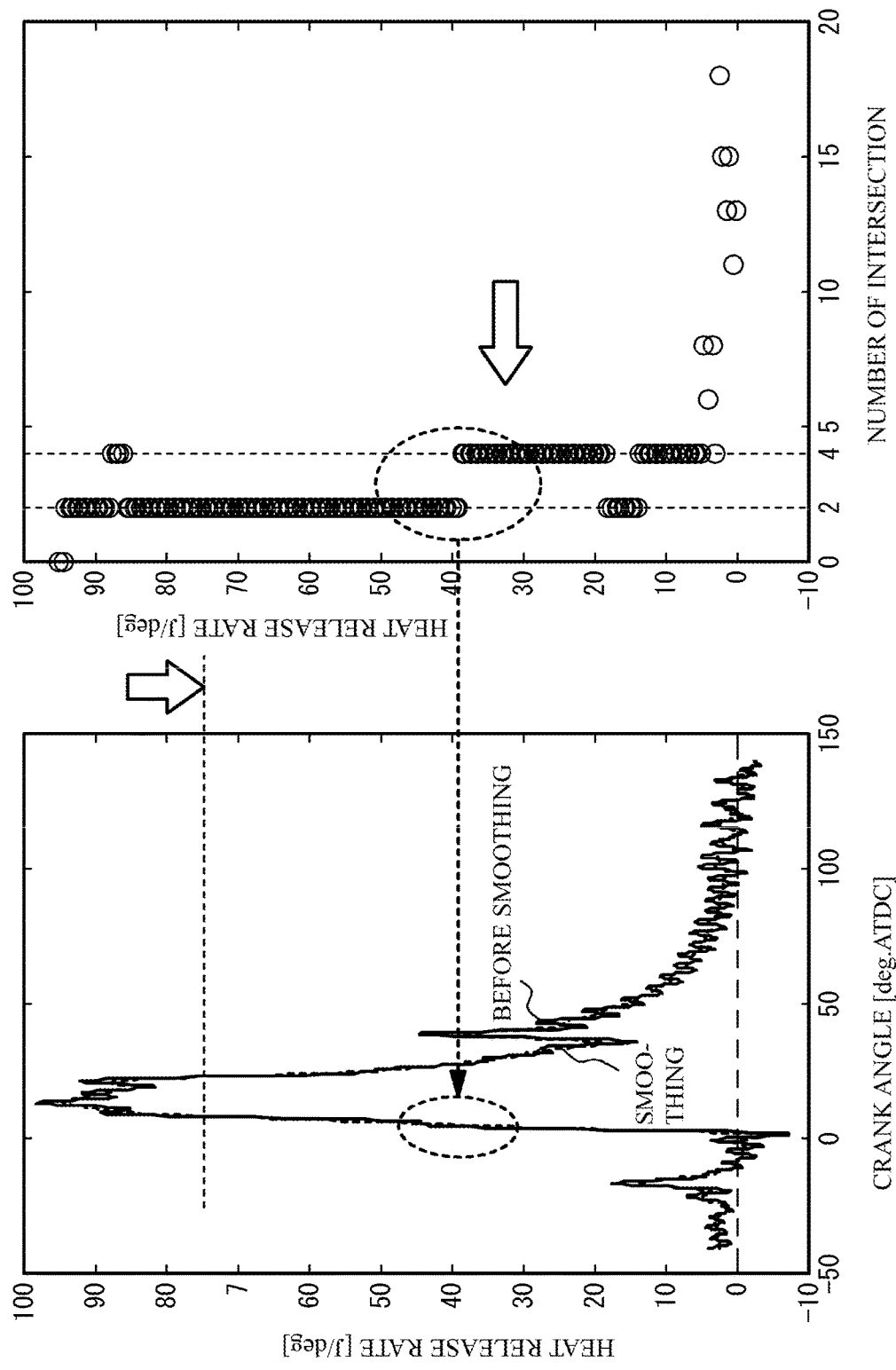
FIG. 10 illustrates intersection between a heat release rate waveform and a straight line.

By setting the first threshold, it is possible to detect a burning (main burning) of which heat release rate is the largest and a burning (after-burning) of which heat release rate is the second largest. By setting the second threshold, it is possible to determine a point in the main burning within a predetermined range of the heat release rate of which reference is a peak of the after-burning. And, it is possible to suppress the influence of noise in the burning (main burning) of which heat release rate is the largest. For example, the first threshold may be 4, and the second threshold may be 6. From the example of the heat release rate waveform of the left of FIG. 10, a result of the intersection analysis of the right figure is obtained. In the example, 40 J/deg of the heat release rate or around is determined as the abdominal part of the main burning. The abdominal part of the main burning corresponds to a predetermined point of the main burning in a predetermined range of the heat release rate of which reference is the peak of the after-burning.

Next, the tangential line calculator 18 calculates a tangential equation (the following formula (5)) at or around one of the abdominal parts of the main burning on the side in which the heat release rate increases with respect to increase of the crank angle and a tangential equation (the following formula (6)) at or around the other of the abdominal parts of the main burning on the side in which the heat release rate decreases with respect to reduction of the crank angle.

$$y_{rhr} = \alpha_{11} \times x_{crank} + \alpha_{10} \quad (5)$$

$$y_{rhr} = \alpha_{21} \times x_{crank} + \alpha_{20} \quad (6)$$

Figure 11:
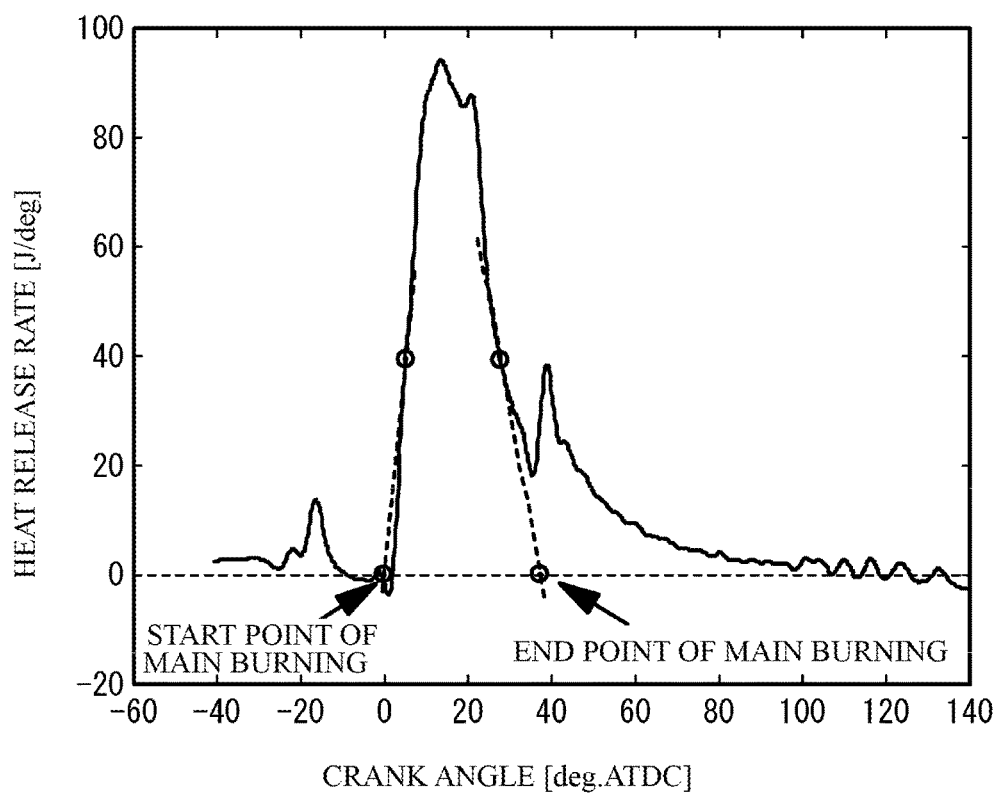
FIG. 11 illustrates tangential lines calculated by a tangential line calculator.

"$\alpha_{11}$" indicates an inclination on the increasing side of the tangential equation. "$\alpha_{10}$" indicates an intercept on the increasing side of the tangential equation. "$\alpha_{21}$" indicates an inclination on the decreasing side of the tangential equation. "$\alpha_{20}$" indicates an intercept on the decreasing side of the tangential equation. FIG. 11 illustrates tangential lines calculated by the tangential line calculator 18.

The calculator 19 to calculate main burning timing calculates a crank angle position at a first predetermined value of the heat release rate as a start timing of the main burning from the tangential equation (5). The calculator 19 to calculate main burning timing calculates a crank angle position at the first predetermined value of the heat release rate as an end timing of the main burning from the tangential equation (6) (Step S14). In the example of FIG. 11, the first predetermined value is set to zero. The first predetermined value for calculating the start timing of the burning may be different from the first predetermined value for calculating the end timing of the burning. The calculator 19 to calculate main burning timing calculates a difference between the end timing of the main burning and the start timing of the main burning, as a main burning period.

Next, the calculator 20 to calculate timing of after-burning obtains a top point of the after-burning by searching the highest heat release rate from the heat release rate waveform from the end timing of the main burning to the opening timing of the exhaust valve (Step S15). The calculator 20 to calculate timing of after-burning determines a position where the heat release rate is reduced by a predetermined ratio from the obtained top point as the abdominal part of the after-burning (Step S16). The calculator 20 to calculate timing of after-burning may determine a position where the heat release rate of the obtained top point is reduced by a predetermined value, as the abdominal part of the after-burning.

Figure 12:
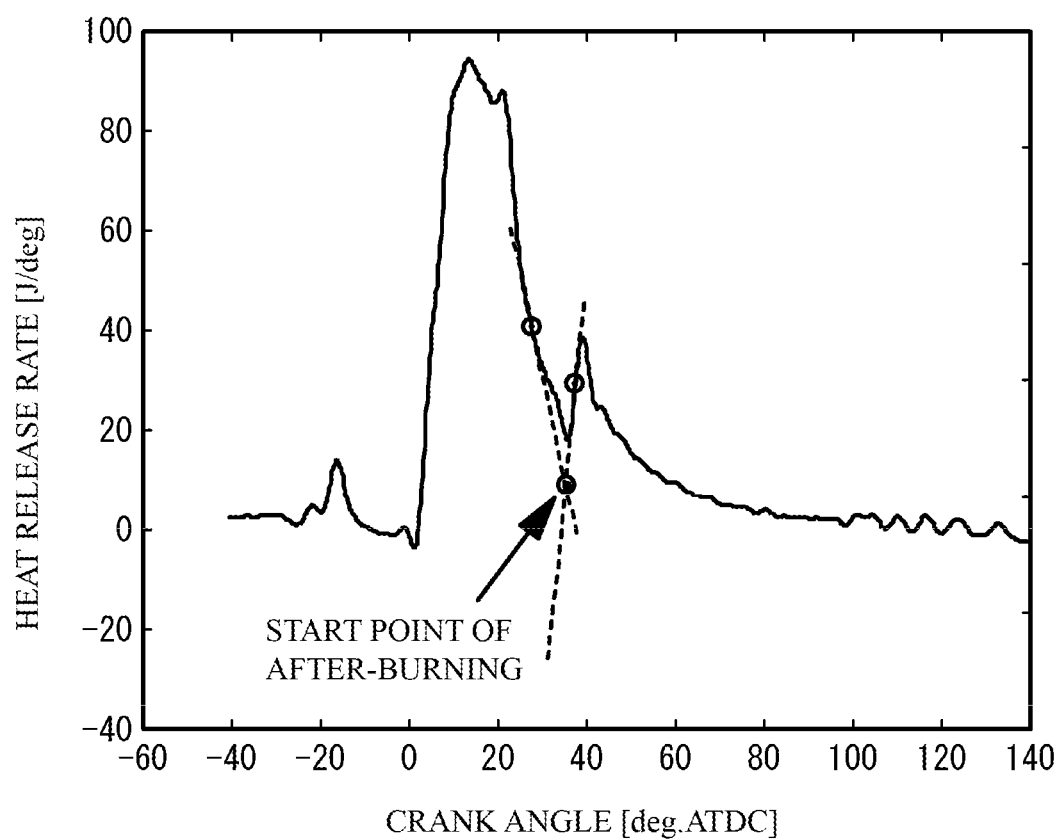
FIG. 12 illustrates a result of calculation of a start timing of an after-burning.

Next, as illustrated in FIG. 12, the tangential line calculator 18 makes a tangential line on the increasing side of the heat release rate waveform at the abdominal part of the after-burning in accordance with the following formula (7) (Step S17). After that, the calculator 20 to calculate after-burning timing calculates an intersection point between a tangential line on the decreasing side of the main-burning (the above-mentioned formula (6)) and the tangential line on the increasing side of the after-burning as the start timing of burning of the after-burning (Step S18).

$$y_{rhr} = \alpha_{31} \times x_{crank} + \alpha_{30} \quad (7)$$

Here, "$\alpha_{31}$" indicates an inclination on the increasing side of the tangential line equation. "$\alpha_{30}$" indicates an intercept on the increasing side of the tangential line equation. FIG. 12 illustrates a result of calculation of the start timing of the after-burning.

Next, the calculator 21 to calculate timing of pre-burning obtains a top point of the pre-burning by searching a point where the heat release rate is the highest from the heat release rate waveform within a range from the opening timing of the inlet valve to the start timing of the main burning (Step S19). The calculator 21 to calculate pre-burning timing determines a point where a predetermined rate of the heat release rate is reduced from the heat release rate of the obtained top point, as the abdominal part of the pre-burning (Step S20). The calculator 21 to calculate pre-burning timing may determine a point where a predetermined value is reduced from the heat release rate of the obtained top point as the abdominal part of the pre-burning.

Figure 13:
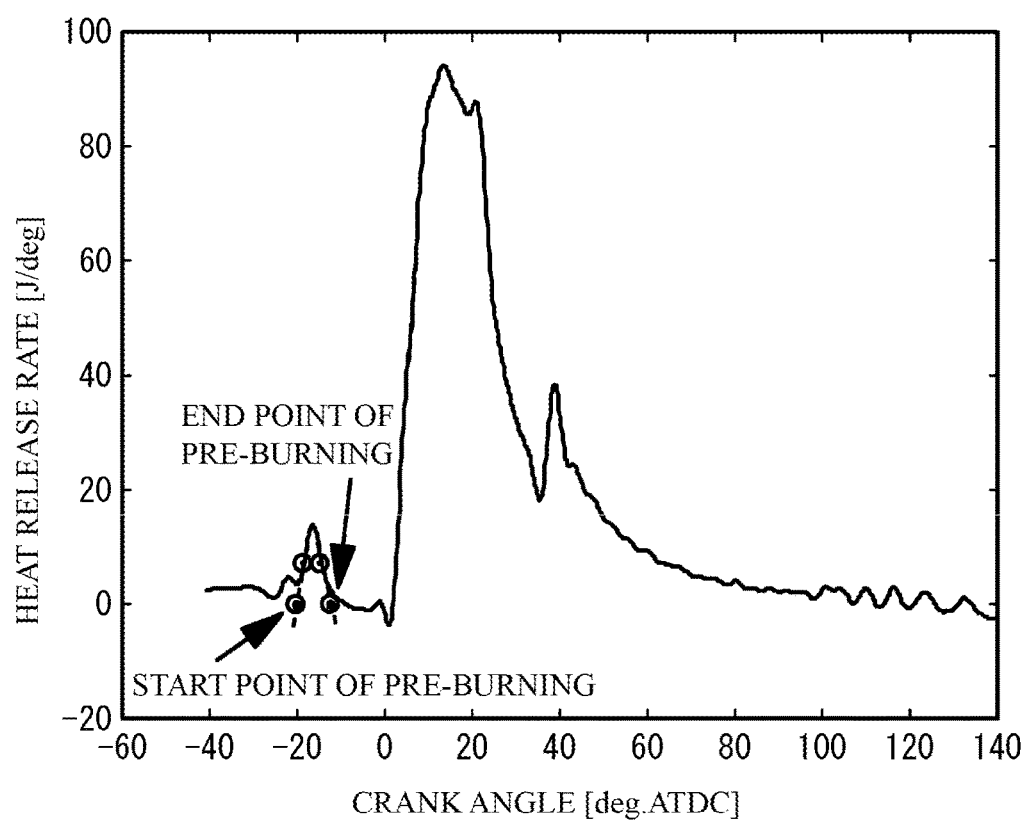
FIG. 13 illustrates a calculation result of a start timing of a pre-burning.

Next, as illustrated in FIG. 13, the tangential line calculator 18 makes a tangential line on the increasing side of the heat release waveform at one of the abdominal parts of the pre-burning (the following formula (8)) and a tangential line of the decreasing side (the following formula (9)) at the other of the abdominal parts.

$$y_{rhr} = \alpha_{41} \times x_{crank} + \alpha_{40} \quad (8)$$

$$y_{rhr} = \alpha_{51} \times x_{crank} + \alpha_{50} \quad (9)$$

"$\alpha_{41}$" indicates an inclination of the tangential line equation. "$\alpha_{40}$" indicates an intercept of the tangential line equation. "$\alpha_{51}$" indicates an inclination of the tangential line equation. "$\alpha_{50}$" indicates an intercept of the tangential line equation.

The calculator 21 to calculate pre-burning timing calculates a crank angle position at a second predetermined value of the heat release rate as the start timing of the pre-burning in the tangential line equation (the above-mentioned equation (8)). The calculator 21 to calculate pre-burning timing calculates a crank angle position at the second predetermined value of the heat release rate as the end timing of the pre-burning in the tangential line equation (the above-mentioned equation (9)). For example, the second predetermined value is set to zero or the like. FIG. 13 illustrates a calculation result of the start timing of the pre-burning. The calculator 21 to calculate pre-burning timing calculates a difference between the start timing of the pre-burning and the end timing of the pre-burning as the pre-burning period (Step S21). The second predetermined value for calculating the start timing of burning may be different from the second predetermined value for calculating the end timing of burning.

Next, as illustrated in FIG. 7, the condition setter 22 sets prior information calculated in advance to an initial value of a model parameter at the identification during the model parameter identification of a heat release rate model including a plurality of Wiebe functions. And, the condition setter 22 sets a limitation condition for searching a predetermined range before and after the value of the prior information (Step S22). The number of prior information may be one or more. The start timing, the end timing and the burning period of the pre-burning and the main burning, and the start timing of the after-burning are used as the prior information. At least one of the start timing and the end timing of the main burning is used as the prior information.

Next, the model parameter identifier 23 identifies the model parameter of the heat release rate model including the plurality of Wiebe functions so that an error of the calculation value of the heat release rate model including a measured value of the heat release rate, the above-mentioned formula (1) and the above-mentioned formula (2) under the setting condition and the limitation condition is reduced (Step S23). It is also possible to use a meta-heuristic numerical solution for searching an approximate solution such as a GA (Genetic Algorithm) or a PSO (Particle Swarm Optimization), as the optimal solver making the above-mentioned error the smallest. In the embodiment, an interior point method is used.

Next, the model parameter storage 24 relates the operation condition obtained from the engine controller 14 with the model parameter calculated by the model parameter identifier 23 and stores the operation condition and the model parameter (Step S24).

The estimation device 13 executes a sequence of processes illustrated in FIG. 8 every predetermined time (for example every 1 second) when the estimation of the heat release rate is requested. The heat release rate estimator 25 obtains a model parameter corresponding to a predetermined operation condition (for example, an operation condition of a current purpose) from the model parameter storage 24 (Step S31). Next, the heat release rate estimator 25 estimates the heat release rate by calculation based on the heat release rate model including the above-mentioned formula (1) and the above-mentioned formula (2) (Step S32).

Figure 14A:
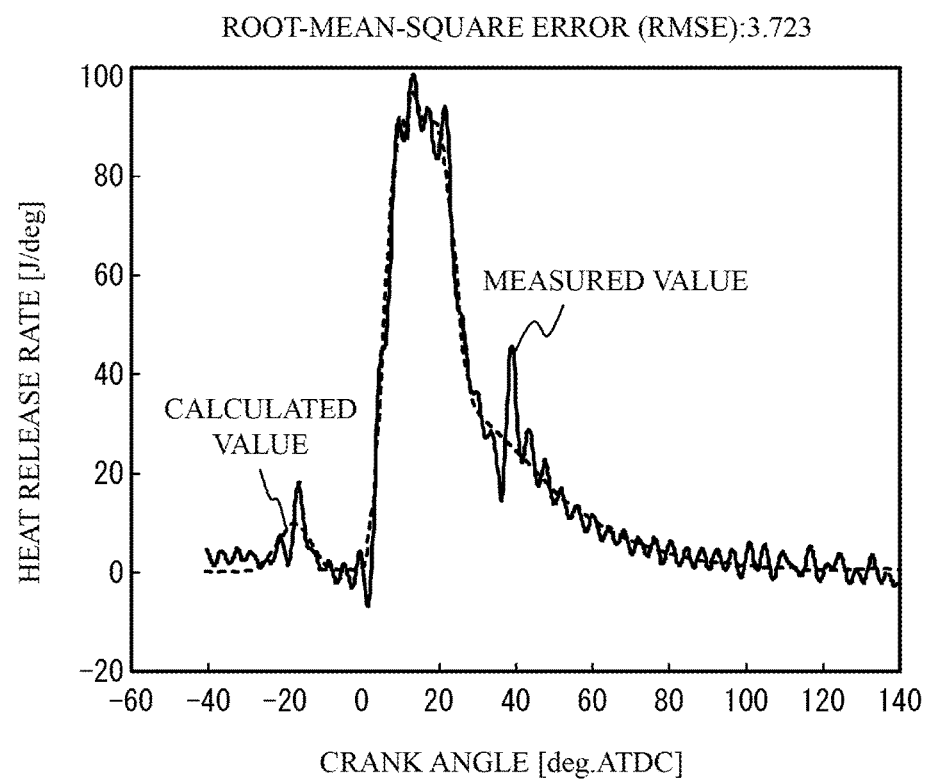
FIG. 14A illustrates an estimation result of a comparative example.
Figure 14B:
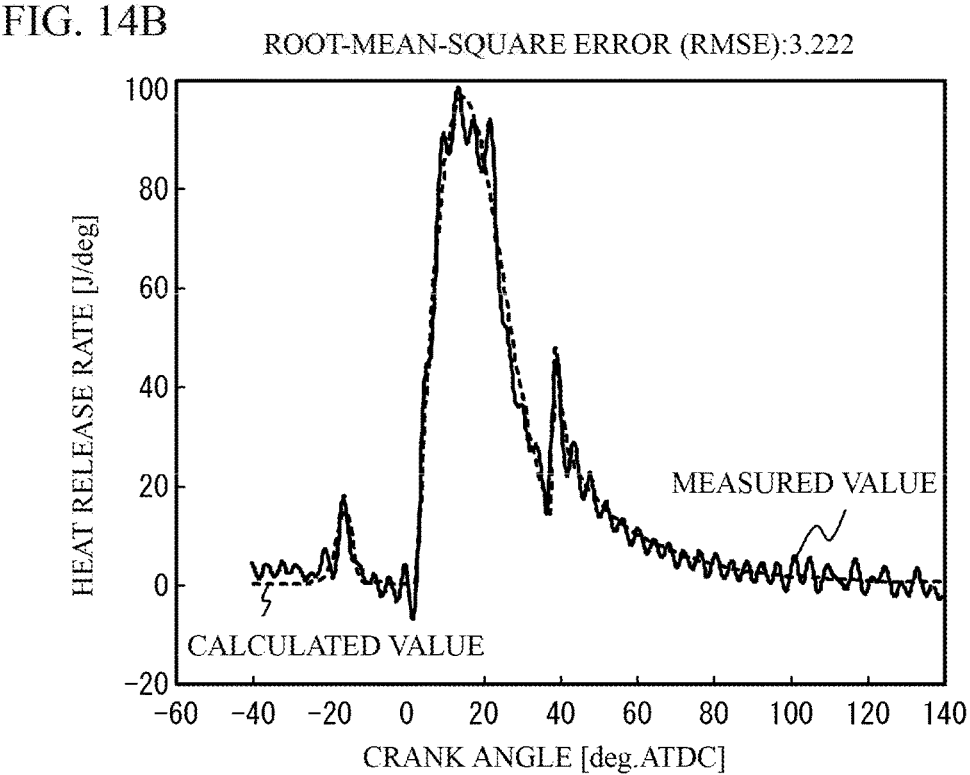
FIG. 14B illustrates an estimation result of an embodiment.

FIG. 14B illustrates the estimation result of the embodiment. FIG. 14A illustrates the result of identification of the heat release rate without getting the above-mentioned prior information as a comparative example. In any of FIG. 14A and FIG. 14B, the heat release rate waveform in the three-stage injection is identified. In the comparative example, a root-mean-square error (RMSE) of the estimation result is 3.723. The RMSE of the estimation result of the method of the embodiment is 3.222. Therefore, the RMSE is reduced by approximately 13%. FIG. 15 illustrates a calculation result of the start timing of the main burning and the start timing of the after-burning of the comparative example and the embodiment. In the comparative example, the start timing of the pre-burning and the start timing of the after-burning are not estimated accurately. However, in the embodiment, it is understood that a value near the true value can be estimated. In the embodiment, 94.7% of error is reduced with respect to the start timing of the main burning and 98.3% of error is reduced with respect to the start timing of the after-burning, compared to the comparative example. In this manner, in the embodiment, it is possible to model each burning part along physical phenomenon. And it is possible to reduce the RMSE by approximately 13%. It is therefore possible to achieve an estimation result of the heat release rate with high accuracy.

In the embodiment, as mentioned above, in a heat release rate waveform of an internal combustion engine in which a plurality of stages of fuel injections are performed, in a predetermined range of a heat release rate having a reference of a peak of a burning having a lower peak, a point is determined in a burning having a higher peak. A tangential line of the heat release rate waveform at the determined point is calculated. And, a predetermined point of the tangential line is set as an initial value for identifying a model parameter of a heat release rate model. When the point (an actual value or a point near the actual value of the start timing of burning or the end timing of burning) of the tangential line is used as the initial value for identifying the model parameter, accuracy of the identification is improved. It is possible to estimate the heat release rate with high accuracy when the model parameter is identified with use of the initial value so that a difference between a calculated value of the heat release rate model and the heat release rate waveform is reduced and the heat release rate corresponding to the operation condition of the internal combustion engine is estimated with use of a result of the determination. When the accuracy of the model is improved, a control performance of a model-based control is improved and fuel cost can be reduced.

In the embodiment, the main burning is used as a burning having a higher peak, and the after-burning is used as a burning having a lower peak. However, the structure is not limited. For example, the main burning may be used as the burning having a higher peak, and the pre-burning may be used as the burning having a lower peak. However, when the after-burning having a relatively higher peak is used as the burning having a lower peak, detection accuracy of the abdominal part of the main burning becomes higher.

When two points on the side in which the heat release rate increases and on the side in which the heat release rate decreases with respect to the increase of the crank angle of the internal combustion engine are determined and a tangential line on at least one of the two points is calculated, a freedom degree of information that can be used as the initial value is enlarged. And two points at which the number of intersections between the heat release rate waveform and the straight line is equal to or more than the second threshold for more than the first threshold period may be identified as the above-mentioned two points, when the predetermined straight line is parallel translated toward lower value from a higher value with a predetermined step size from a value higher than the higher peak of the heat release rate. In this case, it is possible to easily identify the above-mentioned two points. When the smoothing process is performed with respect to the heat release rate waveform and the number of intersections between the heat release rate waveform and the above-mentioned straight line is obtained, the influence of the noise can be suppressed.

When two tangential lines at the above-mentioned two points are calculated and the angle difference (burning period) of the crank angle between predetermined points at the tangential lines are included in the above-mentioned initial value, the accuracy of identification is improved. It is possible to use the start timing or the end timing of the burning having a lower peak when any point on the burning having a higher peak is determined in the heat release rate waveform of the burning having a lower peak, a tangential line at the determined point is calculated, and the initial value includes the intersection between the tangential line and a tangential line on the burning side having a lower peak in the heat release waveform in the burning having the higher peak. Thus, the accuracy of the identification is improved.

In the above-mentioned embodiment, the intersection analyzer 17 acts as a determiner configured to determine a point of a burning having a higher peak in a predetermined range of a heat release rate based on a peak of a burning having a smaller peak, in a heat release rate waveform in an internal combustion engine that performs a multiple-stage fuel injection. The tangential line calculator 18 acts as a tangential line calculator configured to calculate a tangential line of the heat release rate waveform at the point determined by the determiner. The calculator 19 to calculate timing of main burning and the model parameter identifier 23 act as an identifier configured to set a predetermined point on the tangential line as an initial value for identifying a model parameter of a heat release rate model and identify the model parameter so that a difference between a calculation value of the heat release rate model and the heat release rate waveform is reduced with use of the initial value. The heat release rate estimator 25 acts as an estimator configured to estimate a heat release rate corresponding to a predetermined operation condition of the internal combustion engine with a result of an identification of the identifier.

Figure 16:
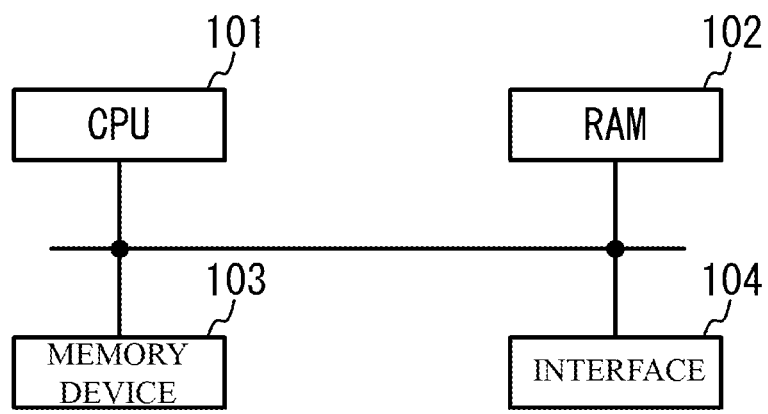
FIG. 16 illustrates a block diagram of a hardware structure of an estimation device.

[Another Example] FIG. 16 illustrates a block diagram of a hardware structure of the estimation device 13. As illustrated in FIG. 16, the estimation device 13 has a CPU 101, a RAM 102, a memory device 103, an interface 104 and so on. The components are connected by a bus or the line. The CPU 101 is a central processing unit. The CPU 101 has one or more cores. The RAM (Random Access Memory) 102 is a volatile memory that temporarily stores a program executed by the CPU 101, a data processed by the CPU 101, and so on. The memory device 103 is a non-volatile storage device. The memory device 103 may be a ROM (Read Only Memory), a solid state drive (SSD) such as a flash memory, or a hard disk driven by a hard disk drive. The memory device 103 stores an estimation program and so on. When the CPU 101 executes the estimation program, the components of the estimation device 13 are established. The estimation device 13 may be a hardware such as a microcomputer, an FPGA, a PLC (Programmable Logic Controller). The components of the estimation device 13 may be dedicated circuits or the like.

The after-burning is an example of a burning after the main burning. Therefore, the after-burning may be a post-burning. The pre-burning is an example of a burning before the main burning. Therefore, the pre-burning may be a pilot-burning before the pre-burning.

In the above-mentioned embodiment, the heat release rate of the three-stage fuel injection is used as an example. A heat release rate of a two-stage fuel injection or a four-stage fuel injection may be used. In any of multiple-stage fuel injection, a point of a burning having a relatively higher peak is determined in a predetermined range of a heat release rate having a reference of a peak of a burning having a relatively lower peak, and a tangential line is calculated at the determined point. And, the point on the tangential line is used as an initial value for identifying a model parameter of a heat release rate model.

Figure 17:
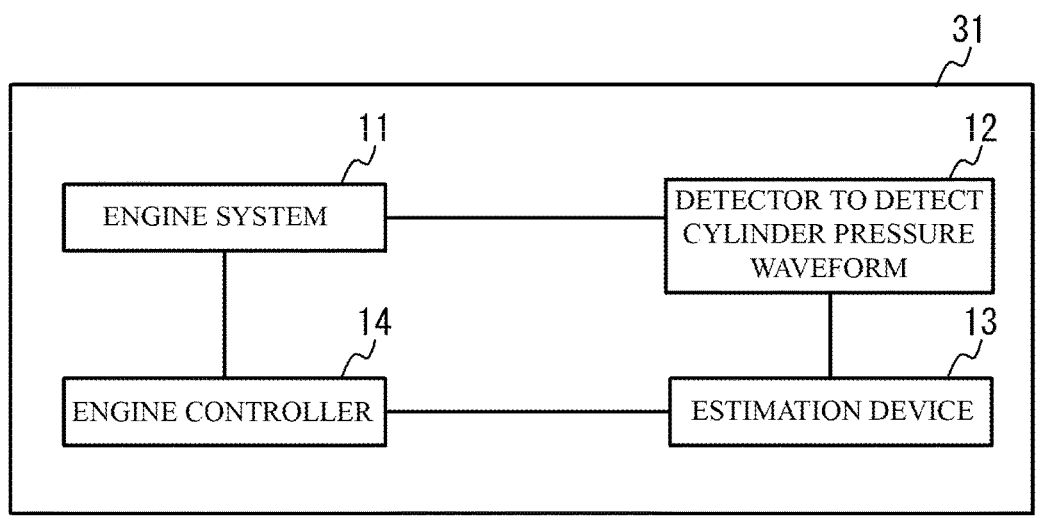
FIG. 17 illustrates an example of a block diagram of a vehicle having an engine to which an estimation device in accordance with an embodiment is applied.

The above-mentioned embodiment is applied to a diesel engine as an example. However, another internal combustion engine such as a gasoline engine may be used. For example, a vehicle 31 such as a passenger car, a track, a ship, a train car, a motorbike, an air plane or a helicopter may have the engine system 11, the cylinder pressure waveform detector 12, the estimation device 13 and the engine controller 14. FIG. 17 illustrates an example of a block diagram of a vehicle having an engine to which the estimation device in accordance with the embodiment is applied.

Figure 18:
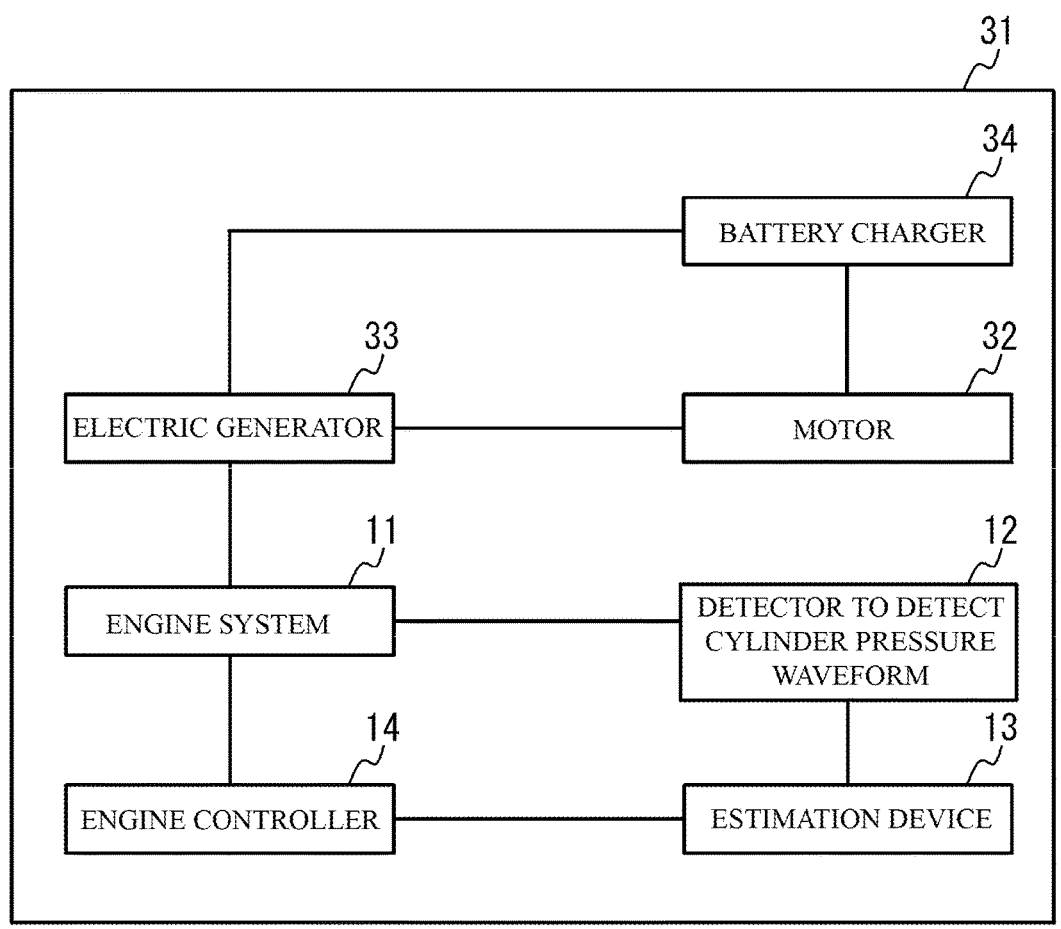
FIG. 18 illustrates an example of a block diagram of a vehicle that has an engine to which an estimation device in accordance with an embodiment is applied, converts kinetic energy of the engine into electrical power by an electrical generator, drives a motor by the electrical power.

FIG. 18 illustrates an example of a block diagram of a vehicle that has an engine to which the estimation device in accordance with the embodiment is applied, converts kinetic energy of the engine into electrical power by an electrical generator, drives a motor by the electrical power. Kinetic energy generated by the engine system 11 may drive the vehicle. An electrical generator 33 may convert the kinetic energy generated by the engine system 11 into electrical power, and a motor 32 may drive the vehicle 31. The electrical power converted by the electrical generator 33 may be accumulated in a battery charger 34, and the accumulated electrical power may drive the motor 32 and may drive the vehicle 31.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various change, substitutions, and alterations could be made hereto without departing from the spirit and scope of the invention.

What is claimed is:

1. An estimation device comprising:
   a memory;
   a processor; and
   a controller configured to control an engine system on a basis of a heat release rate estimated by the processor and an operation condition of an internal combustion engine that performs a multiple-stage fuel injection,
   wherein the processor is configured to execute a process, the process comprising:
   determining a point of a burning having a higher peak in a predetermined range of a heat release rate based on a peak of a burning having a smaller peak, in a heat release rate waveform in the internal combustion engine;
   calculating a tangential line of the heat release rate waveform at the point determined in the determining;
   setting a predetermined point on the tangential line as an initial value for identifying a model parameter of a heat release rate model including a plurality of Wiebe functions;
   identifying the model parameter so that a difference between a calculation value of the heat release rate model and the heat release rate waveform is reduced with use of the initial value; and
   estimating the heat release rate corresponding to a predetermined operation condition of the internal combustion engine with a result of an identification of the identifying,
   wherein:
   in the determining, two points are determined, one of the two points being a point on an increasing side of the heat release rate with respect to an increase of the crank angle of the internal combustion engine, the other of the two points being a point on a decreasing side of the heat release rate with respect to the increase of the crank angle;
   in the calculating, a tangential line of at least one of the two points is calculated; and
   in the determining, a predetermined straight line is parallel translated toward lower values from a higher value with a predetermined step size from a value higher than the higher peak of the heat release rate waveform, and two points at which a number of intersections between the heat release rate waveform and the straight line is equal to or more than a second threshold for more than a first threshold period are determined as the two points.

2. The estimation device as claimed in claim 1, wherein in the determining, the number of intersections between the heat release rate waveform and the straight line is obtained after smoothing the heat release rate waveform.

3. The estimation device as claimed in claim 1, wherein:
in the calculating, tangential lines of the two points are calculated; and
in the identifying, a crank angle difference between predetermined points of the tangential lines is included in the initial value.

4. The estimation device as claimed in claim 1, wherein:
in the determining, a point on a side of the burning having the higher peak is determined, in the heat release rate waveform of the burning having the lower peak;
in the calculating, a tangential line at the point is calculated; and
an intersection between the tangential line and a tangential on a side of the burning having the lower peak in the heat release rate waveform in the burning having the higher peak is included in the initial value.

5. An estimation method comprising:
determining a point of a burning having a higher peak in a predetermined range of a heat release rate based on a peak of a burning having a smaller peak, in a heat release rate waveform in an internal combustion engine that performs a multiple-stage fuel injection;
calculating a tangential line of the heat release rate waveform at the point determined in the determining;
setting a predetermined point on the tangential line as an initial value for identifying a model parameter of a heat release rate model including a plurality of Wiebe functions;
identifying the model parameter so that a difference between a calculation value of the heat release rate model and the heat release rate waveform is reduced with use of the initial value;
estimating a heat release rate corresponding to a predetermined operation condition of the internal combustion engine with a result of an identification of the identifying; and
controlling an engine system on a basis of the heat release rate estimated by the estimating and an operation condition of the internal combustion engine,
wherein:
in the determining, two points are determined, one of the two points being a point on an increasing side of the heat release rate with respect to an increase of the crank angle of the internal combustion engine, the other of the two points being a point on a decreasing side of the heat release rate with respect to the increase of the crank angle;
in the calculating, a tangential line of at least one of the two points is calculated; and
in the determining, a predetermined straight line is parallel translated toward lower values from a higher value with a predetermined step size from a value higher than the higher peak of the heat release rate waveform, and two points at which a number of intersections between the heat release rate waveform and the straight line is equal to or more than a second threshold for more than a first threshold period are determined as the two points.

6. The estimation method as claimed in claim 5, wherein in the determining, the number of intersections between the heat release rate waveform and the straight line is obtained after smoothing the heat release rate waveform.

7. The estimation method as claimed in claim 5, wherein:
in the calculating, tangential lines of the two points are calculated; and
in the identifying, a crank angle difference between predetermined points of the tangential lines is included in the initial value.

8. The estimation method as claimed in claim 5, wherein:
in the determining, a point on a side of the burning having the higher peak is determined, in the heat release rate waveform of the burning having the lower peak;
in the calculating, a tangential line at the point is calculated; and
an intersection between the tangential line and a tangential on a side of the burning having the lower peak in the heat release rate waveform in the burning having the higher peak is included in the initial value.

9. A computer readable, non-transitory medium storing a program that causes a computer to execute a process, the process comprising:
determining a point of a burning having a higher peak in a predetermined range of a heat release rate based on a peak of a burning having a smaller peak, in a heat release rate waveform in an internal combustion engine that performs a multiple-stage fuel injection;
calculating a tangential line of the heat release rate waveform at the point determined in the determining;
setting a predetermined point on the tangential line as an initial value for identifying a model parameter of a heat release rate model including a plurality of Wiebe functions;
identifying the model parameter so that a difference between a calculation value of the heat release rate model and the heat release rate waveform is reduced with use of the initial value;
estimating a heat release rate corresponding to a predetermined operation condition of the internal combustion engine with a result of an identification of the identifying; and
controlling an engine system on a basis of the heat release rate estimated by the estimating and an operation condition of the internal combustion engine,
wherein:
in the determining, two points are determined, one of the two points being a point on an increasing side of the heat release rate with respect to an increase of the crank angle of the internal combustion engine, the other of the two points being a point on a decreasing side of the heat release rate with respect to the increase of the crank angle;
in the calculating, a tangential line of at least one of the two points is calculated; and
in the determining, a predetermined straight line is parallel translated toward lower values from a higher value with a predetermined step size from a value higher than the higher peak of the heat release rate waveform, and two points at which a number of intersections between the heat release rate waveform and the straight line is equal to or more than a second threshold for more than a first threshold period are determined as the two points.

10. The medium as claimed in claim 9, wherein in the determining, the number of intersections between the heat release rate waveform and the straight line is obtained after smoothing the heat release rate waveform.

11. The medium as claimed in claim 9, wherein:
in the calculating, tangential lines of the two points are calculated; and in the identifying, a crank angle difference between predetermined points of the tangential lines is included in the initial value.

12. The medium as claimed in claim 9, wherein:
in the determining, a point on a side of the burning having the higher peak is determined, in the heat release rate waveform of the burning having the lower peak;
in the calculating, a tangential line at the point is calculated; and
an intersection between the tangential line and a tangential on a side of the burning having the lower peak in the heat release rate waveform in the burning having the higher peak is included in the initial value.

13. An engine comprising:
a memory;
a processor;
an engine system; and
a controller configured to control the engine system on a basis of a heat release rate estimated by the processor and an operation condition of an internal combustion engine,
wherein the processor is configured to execute a process, the process comprising:
determining a point of a burning having a higher peak in a predetermined range of a heat release rate based on a peak of a burning having a smaller peak, in a heat release rate waveform in an internal combustion engine that performs a multiple-stage fuel injection;
calculating a tangential line of the heat release rate waveform at the point determined in the determining;
setting a predetermined point on the tangential line as an initial value for identifying a model parameter of a heat release rate model including a plurality of Wiebe functions;
identifying the model parameter so that a difference between a calculation value of the heat release rate model and the heat release rate waveform is reduced with use of the initial value; and
estimating the heat release rate corresponding to a predetermined operation condition of the internal combustion engine with a result of an identification of the identifying,
wherein:
in the determining, two points are determined, one of the two points being a point on an increasing side of the heat release rate with respect to an increase of the crank angle of the internal combustion engine, the other of the two points being a point on a decreasing side of the heat release rate with respect to the increase of the crank angle;
in the calculating, a tangential line of at least one of the two points is calculated; and
in the determining, a predetermined straight line is parallel translated toward lower values from a higher value with a predetermined step size from a value higher than the higher peak of the heat release rate waveform, and two points at which a number of intersections between the heat release rate waveform and the straight line is equal to or more than a second threshold for more than a first threshold period are determined as the two points.

14. A movement device comprising:
a memory;
a processor;
an engine system; and
a controller configured to control the engine system on a basis of a heat release rate estimated by the processor and an operation condition of an internal combustion engine,
wherein the processor is configured to execute a process, the process comprising:
determining a point of a burning having a higher peak in a predetermined range of a heat release rate based on a peak of a burning having a smaller peak, in a heat release rate waveform in an internal combustion engine that performs a multiple-stage fuel injection;
calculating a tangential line of the heat release rate waveform at the point determined in the determining;
setting a predetermined point on the tangential line as an initial value for identifying a model parameter of a heat release rate model including a plurality of Wiebe functions;
identifying the model parameter so that a difference between a calculation value of the heat release rate model and the heat release rate waveform is reduced with use of the initial value; and
estimating the heat release rate corresponding to a predetermined operation condition of the internal combustion engine with a result of an identification of the identifying,
wherein:
in the determining, two points are determined, one of the two points being a point on an increasing side of the heat release rate with respect to an increase of the crank angle of the internal combustion engine, the other of the two points being a point on a decreasing side of the heat release rate with respect to the increase of the crank angle;
in the calculating, a tangential line of at least one of the two points is calculated; and
in the determining, a predetermined straight line is parallel translated toward lower values from a higher value with a predetermined step size from a value higher than the higher peak of the heat release rate waveform, and two points at which a number of intersections between the heat release rate waveform and the straight line is equal to or more than a second threshold for more than a first threshold period are determined as the two points.

* * * * *